United States Patent [19]
Erickson et al.

[11] Patent Number: 5,326,908
[45] Date of Patent: Jul. 5, 1994

[54] PROCESS FOR THE PREPARATION OF ASPARAGINE

[76] Inventors: Robert Erickson, 266 S. Warrington Rd., Des Plaines, Ill. 60016; Ron Bray, 1303 Whitney La., Buffalo Grove, Ill. 60089; Mark Johnson, 17482 W. Windslow, Grayslake, Ill. 60030; Loraine Klein, 331 Somerset Dr., Streamwood, Ill. 60107; Dennis A. Seagle, 610 Checker Dr., Buffalo Grove, Ill. 60089

[21] Appl. No.: 988,052

[22] Filed: Dec. 9, 1992

[51] Int. Cl.$^5$ ............................................. C07C 229/00
[52] U.S. Cl. ..................................................... 562/561
[58] Field of Search ......................................... 562/561

[56] References Cited

U.S. PATENT DOCUMENTS

| | | | |
|---|---|---|---|
| 2,798,092 | 7/1957 | Joyce | 562/561 |
| 3,979,449 | 9/1976 | Hirsbrunner | 562/561 |

OTHER PUBLICATIONS

Greenstein, "Chemistry of the Amino Acids," vol. 2, pp. 924–928 (1961).

Primary Examiner—Michael L. Shippen
Attorney, Agent, or Firm—Jeffrey M. Hoster; Craig M. Bell

[57] ABSTRACT

The present invention is an improved process for the synthesis of asparagine, a non-essential amino acid useful in food and medical applications. The process utilizes mineral acid to make an intermediate beta-methyl aspartate from a reaction mixture of aspartic acid and methanol. The intermediate product is then amminated in situ and asparagine collected with no need for an isolation step of the intermediates.

8 Claims, No Drawings

PROCESS FOR THE PREPARATION OF ASPARAGINE

BACKGROUND OF THE INVENTION

Asparagine is a non-essential amino acid, and specifically is the beta amide of aspartic acid that exists in both the d(+) and l(−) isomeric forms. It is widely distributed in plants and animals as it is found both in free form and as a component in proteins. The amino acid has useful applications as a flavor ingredient, and in medicine and biochemical research. Its chemical formula $NH_2COCH_2CH(NH_2)COOH$ renders it a white crystalline solid that is nearly insoluble in ethanol, methanol, ether and benzene while soluble in acids and alkalies.

L-asparagine synthesis is known by treating beta-methyl-L-aspartate with an alcoholic solution of ammonia, see Beecham A. F., J. Am. Chem. Soc. 76, 4615 (1954). However, this treatment must be run for at least two days in order to obtain acceptable yields. Another article by Miller et. al entitled "The Synthesis of Glutamine and Asparagine Peptides and of Glutamine" teaches the amidation of carbobenzyloxy-L-glutamic acid-gamma-ethyl ester in aqueous ammonia followed by acidification to recover carbobenyoxy-L-glutamine Arch. Biochem. Biophys. 35 176–183 (1952).

U.S. Pat. No. 3,979,499 to Hirsbrunner et. al. discloses the chemical synthesis of asparagine or glutamine from beta-methyl aspartate hydrochloride. The beta methyl aspartate hydrochloride is typically first made by reacting aspartic acid with methanol and hydrochloric acid. See Gmeiner et. al., JOC 55 pp 3068–74. The intermediate is isolated through precipitation with an organic solvent and after the methanol is driven off is reacted with ammonia to yield the final asparagine product.

U.S. Pat. Nos. 2,798,092, 3,105,852 and 2,883,399 all disclose the synthesis of L-glutamine through the esterification and amidation of L-glutamic acid or its derivatives.

The present invention is directed to a novel process for the synthesis of L-asparagine which does away with a number of elements required by synthetic chemical routes known in the art. The absence of these elements enables the synthesis of the amino acid in a far less expensive and hazardous manner.

SUMMARY OF THE INVENTION

The present invention is an improved process for the synthesis of asparagine, a non-essential amino acid useful in food and medical applications. The process utilizes sulfuric acid to make an intermediate beta-methyl aspartate sulfate from a reaction mixture of aspattic acid and methanol. The intermediate product is then treated with ammonia in situ with no need for an isolation step prior to ammonia treatment.

DETAILED DESCRIPTION OF THE INVENTION

An important aspect of the present invention is the realization that sulfuric acid, rather than hydrochloric acid, can be used in the initial esterification reaction with aspattic acid and methanol to produce the beta-methyl aspartate sulfate intermediate which can then be further processed in situ without the need for the additional steps of precipitation with an organic solvent, filtration and isolation. The use of sulfuric acid rather than hydrochloric acid provides a cost savings and allows for the use of a far wider range of materials of construction for the reaction equipment than does hydrochloric acid. Esterification with sulfuric acid rather than hydrochloric acid avoids the necessity of handling anhydrous HCl gas which is considerably more hazardous and difficult to deal with than sulfuric acid. Moreover, the corrosive properties of hydrochloric acid are much greater than those of sulfuric acid and thereby require the use of exotic metals or glass lined equipment in order to carry out the reactions.

Another distinct advantage of the process of the present invention over that of the prior art is the elimination of the isolation step of the beta-methyl aspartate hydrochloride. This avoids the necessity for an additional operation requiring a centrifuge that must be capable of handling flammable organic solvents as well as a solvent recovery operation that requires an evaporator and a distillation column. Overall, these simplications enable the synthesis of asparagine to be carried out with far less investment in equipment and chemicals and allows for a much simpler and safer operation when considered on a large scale industrial basis, these advantages are dramatic.

Aspartic acid, $(HOOCCH_2CH(NH_2)COOH)$ is first reacted with methanol $(CH_3OH)$ and sulfuric acid $(H_2SO_3)$ in a molar ratio range of from at least 1.1/1.0 to about 4/1 sulfuric acid/aspartic acid respectively, and a molar ratio range of at least 1.5/1.0 methanol/aspartic acid with no absolute upper limit, to yield an intermediate beta-methyl aspartate. Ammonia, is added after a sufficient period of time in order to neutralize the sulfuric acid so as to prevent the reaction from proceeding any further than methylation of the beta carbon on the aspartate molecule thereby leaving the alpha carbon unreacted.

The beta-methyl aspartate sulfate is not isolated at this point, but is instead reacted in situ with additional ammonia for the amination of the intermediate compound after excess methanol is evaporated and removed from the system. The ammonia is added in a molar ratio range from about 1:1 to over 200:1 ammonta/aspartic acid. A molar ratio of about 5:1 ammonia/aspartic acid is preferred. Both the amination and stripping of the methanol can be carried out at temperatures from 0° C. to boiling. The application of heat and/or pressure directly affects the rate of reaction and one skilled in the art can Judge accordingly.

After the amination reaction is complete, excess ammonia and water are also removed via distillation or straight evaporation and the crude product is then crystallized by adding acid to adjust the pH to approximately 5.4, the isoelectric point of asparagine, after which the product is then cooled and filtered. In order to better purify the asparagine thus obtained, the compound is dissolved in water with heat and recrystallized as is known in the art. This removes any remaining salt.

All reaction times are dependent upon temperature and any excess of other reactants. The end points for the concentration steps are somewhat arbitrary, and will affect yields and product purities, but these are not critical aspects of the invention.

By doing away with the need for isolating the intermediate, beta-methyl aspartate sulfate, there is not only a cost savings in eliminating the required organic solvent, but this also does away with the requirement of added safety precautions and special equipment that can handle filtration and/or centrifugation of a compound from a flammable organic solvent. This lack of isolation requirement also gives a better yield of product in the first step since no beta-methyl aspartate is lost from the mother liquor. When applied to plant scale applications, these sayings are dramatic.

The following examples are disclosed in order to specifically teach and better define the process of the present invention. It is for illustrative purposes only, and it is realized that minor variations and changes can be made that have not been disclosed or taught herein. Although such changes may not be specifically disclosed, it is to be understood that they fall within the metes and bounds of the present invention as defined by the spirit and scope of the claims that follow:

EXAMPLE 1

A slurry of 66.6 g L-aspartic acid in 295 ml. of methanol was treated with 33 ml. of 98% sulfuric acid, and heated at 50° C. for 3 hours. The solution was cooled to 30° C., and sufficient 17% aqueous ammonia added to adjust the pH to 6.5. The solvent was stripped until the pot temperature reached 75° C. and 60 ml. of water was added. The mixture was then further stripped under vacuum until all of the methanol was removed. Another 50 ml. water was added. The mixture was then cooled to 25° C. and 160 ml. of 17% aqueous ammonia added. The solution was stirred overnight, stripped to an endpoint of 228 grams of residue, cooled to 25° C., and the crude product collected by filtration. The crude product was recrystallized from 70 ml. of water, with pH adjustment to 5.4. The yield of dried asparagine monohydrate was 28.3 grams.

EXAMPLE 2

A solution of 31.5 ml. sulfuric acid in 295 ml. methanol was treated with 66.5 g. L-aspartic acid, and heated at 40–45° C. for 4 hours. The solution was cooled to 24° C., and treated with 28% aqueous ammonia to a pH of 2.5. The mixture was concentrated under vacuum to a thick slurry. The slurry was treated with 750 ml. of 28% aqueous ammonia and 20 ml. water, and stirred at 24° C. for 3.5 hours. The mixture was concentrated under vacuum nearly to dryness, redissolved in 75 ml. water at 55° C., adjusted to pH of 5.4 with excess ammonia, and then cooled to 24° C. The solid was collected by filtration, washed and dried, and finally recrystallized from another 75 ml. water to yield 31.0 g asparagine monohydrate.

What we claim is:

1. A improved process for the preparation of asparagine comprising the steps of:
    a) Preparing a slurry of L-aspartic acid, methanol and mineral acid to yield the beta-methyl aspartate;
    b) Neutralizing said beta-methyl aspartate with a sufficient quantity of aqueous ammonia;
    c) Heating the mixture so as to remove any excess methanol;
    d) Treating the mixture with additional excess ammonia for a sufficient period of time;
    e) Concentrating the solution and adjusting the pH to approximately 5.4; and
    f) Recovering the resulting asparagine monohydrate product.

2. The process of claim 1 wherein said mineral acid is sulfuric acid.

3. The process of claim 2 further comprising recrystallization of said asparagine monohydrate with water.

4. The process of claim 3 wherein said sulfuric acid and said aspattic acid are mixed in a molar ratio range of from about at least 1.1/1.0 to about 4/1 sulfuric acid/aspartic acid, respectively.

5. The process of claim 4 wherein said methanol and said aspattic acid are mixed in a molar ratio of about at least 1.5/1.0 methanol/aspartic acid, respectively.

6. The process of claim 5 wherein said ammonia and beta-methyl aspartate are mixed n molar ratios in a range of from about 1/1 to about 200/1, ammonia/aspartic acid, respectively.

7. A method for the preparation of asparagine, comprising the methylation of aspartic acid in the presence of methanol and sulfuric acid to yield beta-methyl aspartic sulfate, subsequently aminating the intermediate in-situ by the addition of aqueous ammonia and heat to form asparagine monohydrate.

8. The method of claim 7 further comprising the purification and recrystallization of said asparagine monohydrate with water.

* * * * *